United States Patent
McNamara et al.

(10) Patent No.: US 6,395,898 B1
(45) Date of Patent: May 28, 2002

(54) TRANS-GLYCOSIDATION PROCESS FOR THE SYNTHESIS OF (2R, 2-ALPHA-R, 3A)-2-[1-(3,5-BIS(TRIFLUOROMETHYL)PHENYL) ETHOXY]-3-(4-FLUOROPHENYL)-1,4-OXAZINE

(75) Inventors: James M. McNamara, Fanwood; Matthew M. Zhao, Edison, both of NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 09/878,043

(22) Filed: Jun. 8, 2001

Related U.S. Application Data

(60) Provisional application No. 60/210,500, filed on Jun. 9, 2000.

(51) Int. Cl.[7] .............................................. C07D 265/32
(52) U.S. Cl. ......................................................... 544/174
(58) Field of Search ......................................... 544/174

(56) References Cited

U.S. PATENT DOCUMENTS 5,612,337 A * 3/1997 Baker et al. ............. 514/236.2

* cited by examiner

*Primary Examiner*—Robert W. Ramsuer
(74) *Attorney, Agent, or Firm*—J. Eric Thies; Melvin Winokur

(57) ABSTRACT

The present invention is concerned with novel processes for the preparation of (2R, 2-alpha-R, 3a)-2-[1-[3,5-bis(trifluoromethyl)phenyl]ethoxy-3-(4-fluorophenyl)-1,4-oxazine. This compound is useful as an intermediate in the synthesis of compounds which possess pharmacological activity.

16 Claims, No Drawings

TRANS-GLYCOSIDATION PROCESS FOR THE SYNTHESIS OF (2R, 2-ALPHA-R, 3A)-2-[1-(3,5-BIS(TRIFLUOROMETHYL)PHENYL) ETHOXY]-3-(4-FLUOROPHENYL)-1,4-OXAZINE

This application claims the benefit of provisional application No. 60/210,500 filed Jun. 9, 2000.

BACKGROUND OF THE INVENTION

The present invention relates to processes for the preparation of (2R, 2-alpha-R, 3a)-2-[1-[3,5-bis(trifluoromethyl) phenyl]ethoxy-3-(4-fluorophenyl)-1, 4-oxazine which is useful as an intermediate in the preparation of certain therapeutic agents. In particular, the present invention provides a process for the preparation of (2R, 2-alpha-R, 3a)-2-[1-[3,5-bis(trifluoromethyl)phenyl]ethoxy-3-(4-fluorophenyl)-1,4-oxazine which is an intermediate in the synthesis of pharmaceutical compounds which are substance P (neurokinin-1) receptor antagonists.

The general processes disclosed in the art for the preparation of (2R, 2-alpha-R)-4-benzyl-2-[1-[3,5-bis(trifluoromethyl)phenyl]ethoxy-1,4-oxazin-3-one result in relatively low and inconsistent yields of the desired product (see U.S. Pat. No. 5,719,147). In contrast to the previously known processes, the present invention provides more practical and economical methodology for the preparation of (2R, 2-alpha-R, 3a)-2-[1-[3,5-bis(trifluoromethyl)phenyl]-ethoxy-3-(4-fluorophenyl)-1, 4-oxazine in relatively high yield and purity.

It will be appreciated that (2R, 2-alpha-R, 3a)-2-[1-[3,5-bis(trifluoromethyl)phenyl]ethoxy-3-(4-fluorophenyl)-1,4-oxazine is an important intermediate for a particularly useful class of therapeutic agents. As such, there is a need for the development of a process for the preparation of (2R, 2-alpha-R, 3a)-2-[1-[3,5-bis(trifluoromethyl)phenyl] ethoxy-3-(4-fluorophenyl)-1,4-oxazine which is readily amenable to scale-up, uses cost-effective and readily available reagents and which is therefore capable of practical application to large scale manufacture.

Accordingly, the subject invention provides a process for the preparation of (2R, 2-alpha-R, 3a)-2-[1-[3,5-bis (trifluoromethyl)phenyl]ethoxy-3-(4-fluorophenyl)-1,4-oxazine via a very simple, short, relatively inexpensive and highly efficient synthesis.

SUMMARY OF THE INVENTION

The novel process of this invention involves the synthesis of (2R, 2-alpha-R, 3a)-2-[1-[3,5-bis(trifluoromethyl)phenyl] ethoxy-3-(4-fluorophenyl)-1, 4-oxazine. In particular, the present invention is concerned with novel processes for the preparation of a compound of the formula:

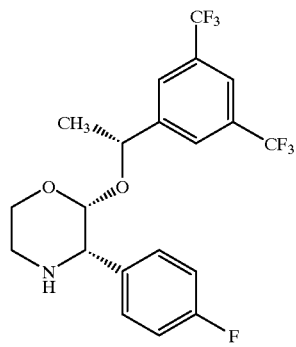

This compound is an intermediate in the synthesis of compounds which possess pharmacological activity. In particular, such compounds are substance P (neurokinin-1) receptor antagonists which are useful e.g., in the treatment of psychiatric disorders, inflammatory diseases, and emesis.

DETAILED DESCRIPTION OF THE INVENTION

The present invention is directed to processes for the preparation of (2R, 2-alpha-R, 3a)-2-[1-[3,5-bis (trifluoromethyl)phenyl]ethoxy-3-(4-fluorophenyl)-1,4-oxazine of the formula:

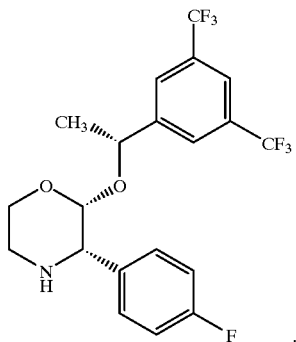

An embodiment of the general process for the preparation of (2R, 2-alpha-R, 3a)-2-[1-[3,5-bis(trifluoromethyl)phenyl] ethoxy-3-(4-fluorophenyl)-1, 4-oxazine of the formula:

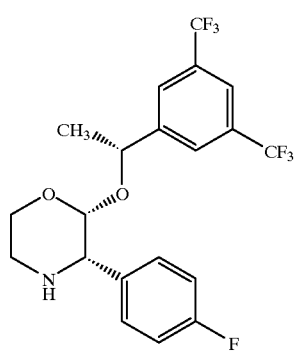

comprises:

(1) contacting a compound of the formula:

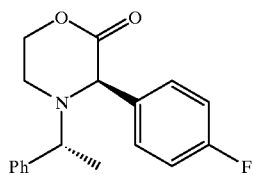

with a reducing agent to give a compound of the formula:

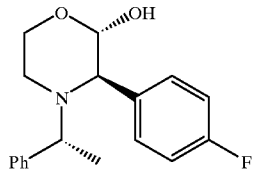

(2) activating such compound with an activating agent to give a compound of the formula:

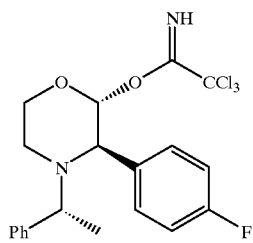

(3) coupling such activated compound with a compound of the formula:

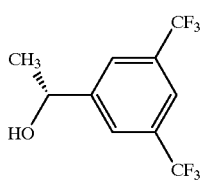

in the presence of a Lewis acid to give a compound of the formula:

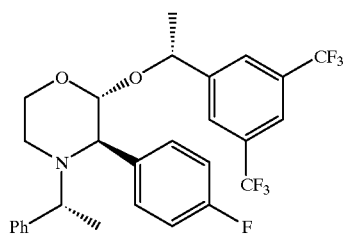

(4) hydrogenation of such compound to give a compound of the formula:

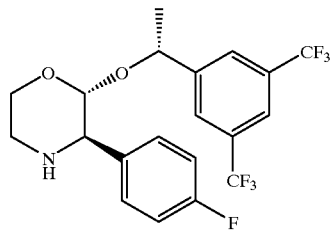

(5) dehydrogenation of such compound to give a compound of the formula:

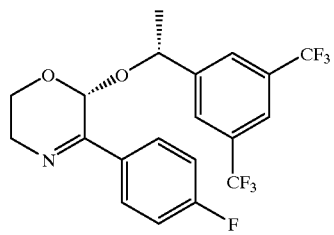

and (6) hydrogenation of such compound to give the compound of the formula:

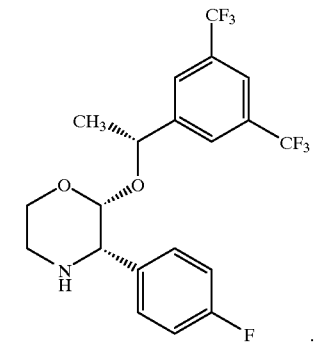

In Step (1) it is preferred that the reducing agent is a hydride reducing agent known in the art and it is more preferred that the reducing agent is di(iso-butyl)aluminum hydride (DIBAL). Preferred solvents for Step (1) comprise an organic solvent which is selected from toluene, tetrahydrofuran (THF), diethyl ether, diglyme, and methyl t-butyl ether, and mixtures thereof, wherein tetrahydrofuran, toluene and mixtures thereof are the more preferred organic solvents. In Step (1) it is preferred that the reaction is between about −70 and 25° C., and preferably about −20° C.

In Step (2) it is preferred that activation of the 2-hydroxy group is conducted via reaction with trichloroacetonitrile to provide the corresponding trichloroimidate (—CNCl$_3$), or alternatively a halogenating agent to provide derivatives substituted with F, Cl, Br, or I, or an optionally substituted alkyl or aryl acid chloride or acid anhydride to provide the corresponding optionally substituted ester (—O—CO—R or —O—COCF$_3$ or —O—COCCl$_3$ wherein R is C$_{1-6}$alkyl, substituted C$_{1-6}$alkyl, phenyl or substituted phenyl).

Preferred activating conditions employ trichloroacetonitrile and a weak base such as potassium carbonate in an organic solvent which is selected from toluene, tetrahydrofuran (THF), diethyl ether, diglyme, and methyl t-butyl ether, and mixtures thereof, wherein tetrahydrofuran, toluene and mixtures thereof are the more preferred organic solvents. Activation is typically carried out at room temperature.

In Step (3) it is preferred that the Lewis acid is selected from boron trifluoride etherate, TMSOTf, titanium tetrachloride, tin tetrachloride, and the like. The solvent is typically an organic solvent which is selected from toluene, tetrahydrofuran (THF), diethyl ether, diglyme, and methyl t-butyl ether, and mixtures thereof, wherein tetrahydrofuran is the more preferred organic solvents The reaction is typically carried out at a temperature range of between about −50 and about 50° C.

In Step (4) it is preferred that the hydrogenation catalyst is a palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst). It is more preferred that the hydrogenation catalyst is palladium on carbon, especially 5% or 10% palladium on carbon. Optionally, the product from Step (3) is contacted with a strong inorganic or organic acid prior to conducting the hydrogenation. The acid is selected from hydrochloric, hydrobromic acid, sulfuric acid, phosphoric acid, formic acid, acetic acid, trifluoroacetic acid, trichloroacetic acid, oxalic acid, tartaric acid, citric acid, malic acid, benzoic acid, 4-nitrobenzoic acid, methanesulfonic acid, trifluoromethane sulfonic acid, benzenesulfonic acid, 4-chlorobenzenesulfonic acid and 4-toluenesulfonic acid, wherein the most preferred acids are hydrochloric acid, hydrobromic acid or 4-toluenesulfonic acid. It is preferred that the solvent for the hydrogenation comprises a solvent which is selected from the group of $C_1$–$C_4$ primary, secondary and tertiary alcohols, and water. Preferred solvents for the hydrogenation comprise methanol, ethanol, isopropanol, n-propanol, n-butanol, water, and mixtures thereof. More preferred solvents for the hydrogenation comprise methanol and mixtures of methanol and water. It is preferred that the temperature of the reaction mixture for the hydrogenation is from about 10° C. to about 50° C., wherein the most preferred temperature is about 20–25° C. It is preferred that the pressure of hydrogen during the hydrogenation is from about 1 to about 150 psi, wherein the most preferred pressure is about 5 to about 50 psi.

In Step (5) the dehydrogenation is conducted under dehydrogenating conditions such as dibromouricil (DBU) and N-chlorosuccinimide. The solvent typically comprises a polar aprotic solvent, such as selected from acetonitrile, dimethylformamide, ethyl acetate, tetrahydrofuran, toluene, dichloromethane and the like. A preferred solvent is dimethylformamide. The reaction is typically carried out at a temperature range of between about −50 and about 50° C. and preferably about 0° C.

In Step (6) it is preferred that the hydrogenation catalyst is a palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst). It is more preferred that the hydrogenation catalyst is palladium on carbon, especially 5% or 10% palladium on carbon. It is preferred that the solvent for the hydrogenation comprises a solvent which is selected from the group of $C_1$–$C_4$ primary, secondary and tertiary alcohols, and water. The solvent may also comprise a polar aprotic solvent selected from acetonitrile, dimethylformamide, ethyl acetate, tetrahydrofuran, toluene, dichloromethane and the like (such as may be present from the previous Step (5). Preferred solvents for the hydrogenation comprise methanol, ethanol, isopropanol, n-propanol, n-butanol, water, and mixtures thereof. More preferred solvents for the hydrogenation comprise methanol and mixtures of methanol and water. It is preferred that the temperature of the reaction mixture for the hydrogenation is from about 10° C. to about 50° C., wherein the most preferred temperature is about 20–25° C. It is preferred that the pressure of hydrogen during the hydrogenation is from about 1 to about 150 psi, wherein the most preferred pressure is about 5 to about 50 psi.

An embodiment of the present invention concerns a process for the preparation of (2R, 2-alpha-R, 3a)-2-[1-[3,5-bis(trifluoromethyl)phenyl]ethoxy-3-(4-fluorophenyl)-1,4-oxazine of the formula:

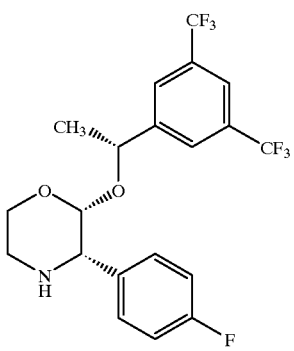

which is outlined as follows:

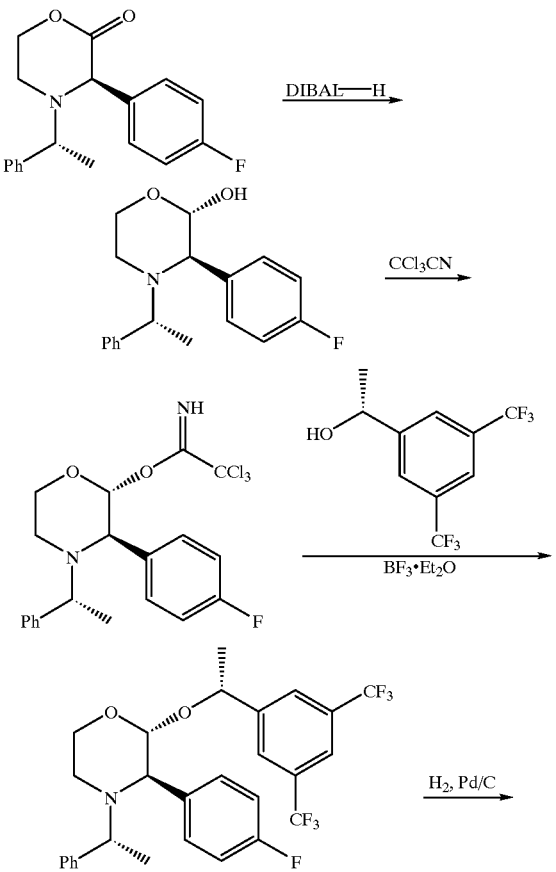

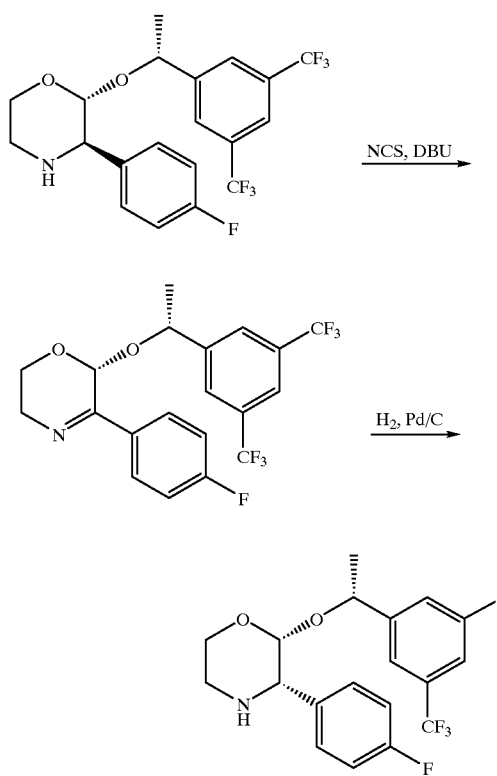

Another embodiment of the present invention concerns a process for the preparation of a compound of the formula:

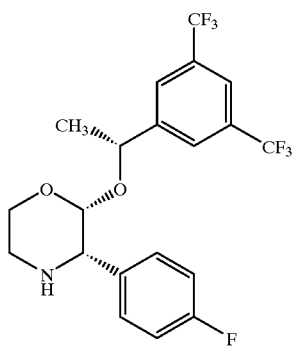

which comprises hydrogenation of a compound of the formula:

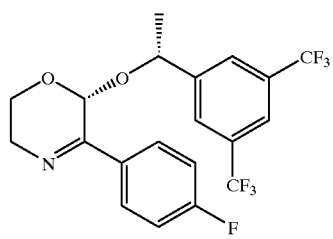

to give the compound of the formula:

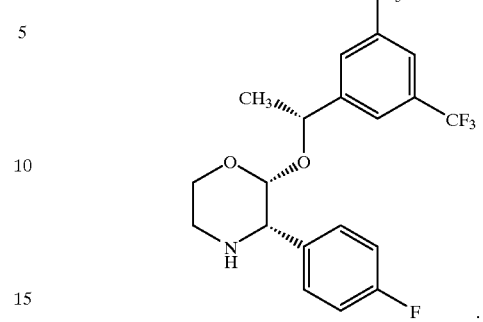

In this embodiment it is preferred that the hydrogenation is catalytic hydrogenation. It is preferred that the hydrogenation catalyst is a palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst). It is more preferred that the hydrogenation catalyst is palladium on carbon, especially 5% or 10% palladium on carbon. It is preferred that the solvent for the hydrogenation comprises a solvent which is selected from the group of $C_1$–$C_4$ primary, secondary and tertiary alcohols, and water. Preferred solvents for the hydrogenation comprise methanol, ethanol, isopropanol, n-propanol, n-butanol, water, and mixtures thereof. More preferred solvents for the hydrogenation comprise ethanol or methanol and mixtures thereof with water. It is preferred that the temperature of the reaction mixture for the hydrogenation is from about 10° C. to about 50° C., wherein the most preferred temperature is about 20–25° C. It is preferred that the pressure of hydrogen during the hydrogenation is from about 1 to about 150 psi, wherein the most preferred pressure is about 5 to about 50 psi.

The (2R, 2-alpha-R, 3a)-2-[1-[3,5-bis(trifluoromethyl) phenyl]ethoxy-3-(4-fluorophenyl)-1,4-oxazine obtained in accordance with the present invention may be used as starting material in further reactions directly or following purification.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

4-Benzyl-2-hydroxy-1,4-oxazin-3-one

4-Benzyl-2-hydroxy-1,4-oxazin-3-one

| Materials | MW | Density | Amount | mol | Equiv. |
|---|---|---|---|---|---|
| N-Benzylethanolamine (96%) | 151.21 | 1.065 | 7.80 kg | 49.5 (assay) | 1.0 |
| Glyoxylic acid (50% in water) | 74.04 | 1.342 | 12.60 L | 114.2 | 2.31 |
| Tetrahydrofuran | 72.11 | 0.889 | 27.0 L | — | — |
| 4-Benzyl-2-hydroxy-1,4-oxazin-3-one seed | 207.23 | — | 0.252 kg | 1.24 | 0.025 |
| Water | 18.0 | 1.00 | 63.0 L | — | — |

A solution of THF (27.0 L) and 50% aqueous glyoxylic acid (12.6 L; 16.9 kg) was heated to reflux and N-benzylethanolamine (7.8 kg) was added over 45 min. The resulting mixture was refluxed for 21 h. Then the THF was distilled under atmospheric pressure while maintaining a constant volume by simultaneous addition of water (27 L). Upon completion of the distillation (<8 vol % of THF in batch) the mixture was cooled from approximately 95–100 to 79–81° C. and was optionally seeded with 4-benzyl-2-hydroxy-1,4-oxazin-3-one (250 g). Upon further cooling to room temperature the product crystallized. Crystalline 4-benzyl-2-hydroxy-1, 4-oxazin-3-one was filtered, washed with water and then dried in a vacuum oven at about 60° C. under a stream of $N_2$ (72–76% yield); m.p. 134° C. $^1$H NMR (400 MHz, $CDCl_3$)δ3.11 (ddd, J=12.5, 3.6 2.4 Hz, 1H), 3.45 (ddd, J=12.5, 10.8, 4.4 Hz, 1 H), 3.78 (ddd, J=12.1, 4.4, 2.4 Hz, 1H),4.29 (ddd, J=12.1, 10.8, 3.6 Hz, 1H), 4.51 (d, J=14.5 Hz, 1H), 4.73 (d, J=14.5 Hz, 1H), 5.40 (s, 1H), 5.76 (br s, 1H), 7.26–7.37 (m, 5H); $^{13}$C NMR (100 MHz, $CDCl_3$) δ45.6, 49.9, 57.6, 90.5, 127.9, 128.3 (2C), 128.9 (2C), 135.6, 167.3 $^1$H NMR [400 MHz, $(CD_3)_2SO$]δ3.10 (ddd, J=12.4, 3.8 2.0 Hz, 1H), 3.34 (ddd, J=12.4, 11.2, 4.8 Hz, 1 H), 3.68 (ddd, J=12.0, 4.8, 2.0 Hz, 1H), 4.10 (ddd, J =12.0, 11.2, 3.8 Hz, 1H), 4.46 (d, J=14.8 Hz, 1H), 4.55 (d, J=14.8 Hz, 1H), 5.06 (d, J=6.2 Hz, 1H), 7.15 (d, J=6.2 Hz, 1-OH), 7.23–7.36 (m, 5H); $^{13}$C NMR [100 MHz $(CD_3)_2SO$]δ46.0, 49.1, 56.6, 90.6, 127.8, 128.1 (2C), 129.0 (2C), 137.2, 166.2.

EXAMPLE 2

3,5-Bis(trifluoromethyl)bromobenzene 3,5-Bis(trifluoromethyl)bromobenzene

| Materials | MW | Density | Amount | Mmol | Equiv. |
|---|---|---|---|---|---|
| 1,3-Bis(trifluoromethyl)benzene | 214.1 | 1.38 | 107 g | 500 | 1.0 |
| 96% $H_2SO_4$ | | | 142 mL | | |
| Glacial HOAc | | | 22 mL | | |
| 1,3-Dibromo-5,5-dimethylhydantoin | 285.93 | | 77.25 g | 270 | 1.08 ($Br^+$) |
| 5N Aq NaOH | | | 75 mL | | |

A vigorously stirred solution of 1,3-bis(trifluoromethyl)benzene (107 g) in a mixture of glacial acetic acid (22 mL) and concentrated sulfuric acid (142 mL) was added 1,3-dibromo-5,5-dimethylhydantoin (77.25 g) at 25° C. The exothermic reaction raised the temperature to approximately 40° C. After aging at 45° C. for 4.5 h, the mixture was cooled to approximately 0° C. and poured into cold water (250 mL). After washing with 5N NaOH (75 mL) the organic layer contained 137 g of the desired 3,5-bis(trifluoromethyl)-1-bromobenzene by assay (94% yield). This product was used in the next step without further purification.

EXAMPLE 3

1-(3,5-Bis(trifluoromethyl)phenyl)ethan-1-one 1-(3,5-Bis(trifluoromethyl)phenyl)ethan-1-one

| Materials | MW | Density | Amount | Mmol | Equiv |
|---|---|---|---|---|---|
| 3,5-Bis(trifluoromethyl)bromobenzene | 293.03 | 1.699 g/L | 29.3 g | 98.0 | 1.0 |
| Magnesium granules, 20 mesh | 24.3 | | 5.10 g | | 2.1 |

-continued 1-(3,5-Bis(trifluoromethyl)phenyl)ethan-1-one

| Materials | MW | Density | Amount | Mmol | Equiv |
|---|---|---|---|---|---|
| Acetic Anhydride | 102.1 | 1.08 g/L | 40 mL | 423 | 4.5 |
| THF (KF = 60 μg/mL) | | | 260 mL | | |
| MTBE | | | 650 mL | | |
| Water | | | 300 mL | | |
| 50% NaOH | | | 40 mL | | |

A solution of 3,5-Bis(trifluoromethyl)bromobenzene (29.3 g) in 30 mL of THF was added to a mixture of magnesium granules (5.10 g) in THF (200 mL) heated at reflux (the reaction was initiated with approximately 5 mL of the bromide solution; the remainder was added slowly over 1 h). The mixture was aged for 30 min at reflux, cooled to RT and added over 1 h to a solution of acetic anhydride (40 mL) in THF (40 mL) maintained at −15° C. The resulting dark brown mixture was warmed to 10° C. in a water bath, and water (300 mL) was added. The pH of the vigorously stirred biphasic mixture was adjusted to 8.0 using 50% NaOH. MTBE (300 mL) was added, the layers were separated and the aqueous layer was further extracted with MTBE (3×150 mL). The organic layers were combined and concentrated in vacuo (bath at 30–35° C.; 50–80 torr). The concentrate was then distilled at atmospheric pressure to provide the pure product (20.7 g; 82% yield) with a boiling point of 187–189° C.

EXAMPLE 4

(R)-1-(3,5-Bis(trifluoromethyl)phenyl)ethan-1-ol

| (R)-1-(3,5-Bis(trifluoromethyl)phenyl)ethan-1-ol | | | |
|---|---|---|---|
| 1-(3,5-Bis(trifluoromethyl)-phenyl)ethan-1-one | 256.15 | 3.9 | 1 Kg |
| (Cp*RhCl₂)₂ (Cp* = Pentamethylcyclopentadienyl) | 618.08 | 0.01 | 6 g |
| (S,R)-cis-Aminoindanol | 149.20 | 0.02 | 3.0 g |
| NaOH | 5 N (H₂O) | 0.05 | 9 mL |
| IPA | | | 7 L |
| HCl | 1 N (H₂O) | | 7 L |
| Heptane | | | 7 L |
| 1,4-diazabicyclo[2.2.2]octane (DABCO) | 112.18 | 2.2 | 240 g |

A solution of [Cp*RhCl₂]₂ (Cp* = pentamethylcyclopentadienyl; 6.0 g), (1S,2R)-cis-1-amino-2-indanol (3.0 g) and 1-(3,5-Bis(trifluoromethyl)phenyl)ethan-1-one (1.0 kg) in 2-propanol (7 L) was stirred for 30 min and thoroughly degassed under vacuum. Then 5 M sodium hydroxide (9 mL) was added and the mixture was aged for 3–4 h to achieve complete conversion of the starting material. The reaction mixture was poured into 1 N HCl (7 L) and extracted with heptane (2×3.5 L). The combined organic layers were washed with brine (5 L) and 1,4-diazabicyclo[2.2.2]-octane (240 g) was added. The solution was concentrated to approximately 4 mL/g of alcohol (KF<200 μg/mL; 2-propanol<5 vol %). The mixture was seeded at 40° C., allowed to cool to RT to from a seedbed and then cooled to 0° C. The crystalline product was filtered, washed with cold heptane and dried to provide the DABCO complex (70% yield; e.e.>99%).

EXAMPLE 5

(R)-1-(3,5-Bis(trifluoromethyl)phenyl)ethan-1-ol

| (R)-1-(3,5-Bis(trifluoromethyl)phenyl)ethan-1-ol | | | |
|---|---|---|---|
| Materials | MW | Mol | Amt |
| 1-(3,5-Bis(trifluoromethyl)-phenyl)ethan-1-one | 256.15 | 11.7 | 3 Kg |
| [RuCl₂(p-cymene)]₂ (Cym = p-cymene (4-isopropyltoluene)) | 612.40 | 0.03 | 18.4 g |
| (S,R)-cis-Aminoindanol | 149.20 | 0.06 | 9.0 g |
| NaOH | 5 N (H₂O) | 0.14 | 28 mL |
| IPA | | | 21 L |
| HCl | 1 N (H₂O) | | 21 L |
| Heptane | | | 21 L |
| 1,4-Diazabicyclo[2.2.2]octane (DABCO) | 112.18 | ~6.6 | ~740 g |

A solution of [RuCl₂(p-cymene)]₂ (18.4 g), (1S, 2R)-cis-1-amino-2-indanol (9.0 g) and 1-(3,5-bis(trifluoromethyl)phenyl)ethan-1-one (3 kg) in 2-propanol (21 L) was stirred for 30 min and thoroughly degassed under vacuum. Then 5 M sodium hydroxide (28 mL) was added and the mixture was aged for 4–6 h to achieve complete conversion of the starting material. The reaction mixture was poured into 1 N HCl (21 L) and extracted with heptane (2×10.5 L). The combined organic layers were washed with brine and 1,4-diazabicyclo[2.2.2]octane (740 g) was added. The solution was concentrated to approximately 4 mL/g of alcohol (KF<200 μg/mL; 2-propanol <5 vol %). The mixture was seeded at 40° C., allowed to cool to RT to from a seedbed and then cooled to 0° C. The crystalline product was filtered, washed with cold heptane and dried to provide the DABCO complex (75–80% yield; e.e.>99%).

EXAMPLE 6
Preparation of N-((S)-(-)-α-Methylbenzyl)-3-(S)-(4-fluorophenyl)-1, 4-oxazin-2-one hydrochloride from 4-Fluorophenylglyoxal hydrate and (S)-2-(1-Phenylethyl)-ethanolamine (Process A)

A mixture of 2-(1-(S)-phenylethyl)ethanolamine([CAS 66849-29-4], 5 g, 30 mmol), 4-fluorophenylglyoxal hydrate (5.7 g, 33 mmol) and acetic acid (10 ml) in isopropyl acetate (50 ml) was heated under reflux for 2.5 hours. The mixture was cooled, diluted with isopropyl acetate (100 ml) and washed with water (2×50 ml), aqueous sodium bicarbonate (2×50 ml) then water (25 ml). The solution was filtered then concentrated to low volume by distillation in a vacuum at 50° C.

The mixture was flushed with isopropyl acetate (2×100 ml) and the final volume adjusted to 150 ml with isopropyl acetate. The solution was heated to reflux temperature and saturated with HCl gas. After 8 hours the resultant slurry was cooled to room temperature and the product collected by filtration and washed with isopropyl acetate (50 ml). The product was dried in a vacuum at 50° C. to give N-((S)-(-)-α-methylbenzyl)-3-(S)-(4-fluorophenyl)-1,4-oxazin-2-one hydrochloride as a white crystalline solid. (8.76 g) (99% recovery from crude free base) 97.4% d.e. by HPLC, m.p. 202–204° C.

EXAMPLE 7
Preparation of N-((S)-(-)-α-Methylbenzyl)-3-(S)-(4-fluorophenyl)-1,4-oxazin-2-one hydrochloride from 4-Fluorobenzaldehyde and (S)-(α-Methylbenzylethanolamine (Process B)

A solution of 4-fluorobenzaldehyde (12.4 g) in methanol (3.6 ml) was added to a solution of sodium metabisulfite (10.3 g) in water (86 ml). Sodium cyanide (5.1 g) was added and the mixture stirred for 60 minutes at ambient temperature. A solution of (S)-α-methylbenzylethanolamine (18.34 g) in methanol (20 ml) was added and the mixture was heated at 30° C. overnight, then at 40° C. for 3 hours and 50° C. for 3 hours. The mixture was cooled and partitioned between water (41 ml) and isopropyl acetate (107ml). The organic extract was washed with water (2×41 ml) and dried by azeotropic distillation.

A solution of HCl gas in isopropyl acetate (10% w/v, 36.5 ml) was added, followed by water (0.36 g), followed by a solution of HCl gas in isopropyl acetate (10% w/v, 36.5 ml). The mixture was stirred for 3 days then filtered to isolate the title compound (11.7 g) (??% recovery from crude free base) 97.6% d.e. by HPLC.

EXAMPLE 8
Preparation of N-((S)-(-)-α-Methylbenzyl)-3-(S)-(4-fluorophenyl)-1,4-oxazin-2-one hydrochloride from 4-Fluorobenzaldehyde and (S)-(α-Methylbenzylamine (Process C)

A solution of 4-fluorobenzaldehyde (1.02 kg, 8.2 mol) in methanol (1 l) was added to a solution of sodium metabisulfite (842 g) in water and aged for 30 minutes. Sodium cyanide (414 g) was added and rinsed in with water (400 ml). After 45 minutes a solution of (S)-α-methylbenzylamine (1.0 kg) in methanol (600 ml) was added and the mixture was aged overnight at room temperature. The mixture was partitioned between water (3.5 l) and isopropyl acetate (5 l). The organic phase was washed with water (3.5 l) and concentrated in a vacuum. The residue was dissolved in dimethylsulfoxide (7.6 l) and potassium carbonate (444 g) added. 27% aq. Hydrogen peroxide (1.28 l) was added over 30 minutes at <30° C. The mixture was then heated overnight at 40° C. The mixture was partitioned between water (16 l) and isopropyl acetate (11 l). The organic layer was washed with water (2×4.5 l) and concentrated to an oil (2.14 kg, 96%). This crude amide was dissolved in IMS (4 l) and a solution of sodium hydroxide (460 g) in water (11.3 l) was added. The solution was heated under reflux for 12 hours then concentrated by distillation to remove IMS. The mixture was washed with ethylene glycol (2×2.2 l) and the aqueous layer was acidified to pH 6.5 with aqueous HCl. The product, N-((S)-(α-methylbenzyl)-4-fluorophenylglycine (1.7 kg, 75% yield from 4-fluorobenzaldehyde) was isolated by filtration. N-((S)-αmethylbenzyl)-4-fluorophenylglycine (1.4 kg), diisopropylethylamine (1.99 l, 2.2 eq.) and 1,2-dibromoethane (3.78 l, 8.5 eq.) were combined in dimethylformamide (24.5 l) and heated at 125° C. for 8 hours. The mixture was concentrated in a vacuum and partitioned between isopropyl acetate (15 l) and water (15 l). The organics were washed with water (15 l) and evaporated to give the crude oxazinone as a dark-coloured oil (1.44 kg).

The dark oil was dissolved in isopropyl acetate (10.4 l) and heated to 85° C. HCl gas was bubbled though the mixture at 80–85° C. for 6 hours, the flow stopped and the mixture allowed to cool slowly to 23° C. The slurry was filtered and the solid was washed with isopropyl acetate. The solid was dried to give N-((S)-(-)-(α-methylbenzyl)-3-(S)-(4-fluorophenyl)-1,4-oxazin-2-one hydrochloride as a light brown solid (970 g) (83% recovery from crude free base) d.e. 98.4% by HPLC.

EXAMPLE 9

N-((S)-(-)-α-Methylbenzyl)-2-hydroxy-3-(S)-(4-fluorophenyl)-1,4-oxazin-2-one

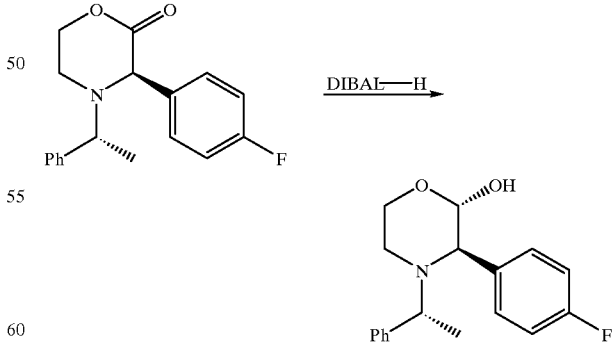

To a slurry of N-((S)-(-)-α-methylbenzyl)-3-(S)-(4-fluorophenyl)-1, 4-oxazin-2-one hydrochloride (1.0 kg) in toluene (4.0L) was added a saturated NaHCO₃ solution (3.5 L). The mixture was stirred until all the solids had dissolved. The organic layer was separated and washed with water (2.5

L), brine (2.5 L) and concentrated to a volume of approximately 3.0 L. THF (2.5 L) was added and the resulting solution was cooled to −20° C. A solution of DIBAL-H in toluene (25 w %, 1.5 M, 2.08 L) was added over 2 h. The mixture was aged for 30 min, quenched with a saturated solution of Rochelle salt (2.5 L) at 0–20° C. and then aged at RT for another 2–5 h. The organic layer was separated, washed with 1/1 mixture of water and brine (2×2.5 L) and concentrated to a volume of approximately 3.8 L. This crude lactol solution (KF<100 μg/mL) was used directly for the next step.

EXAMPLE 10

Formation of Trichloroimidate of N-((S)-(-)-α-Methylbenzyl)-2-hydroxy-3-(S)-(4-fluorophenyl)-1,4-oxazine-2-one

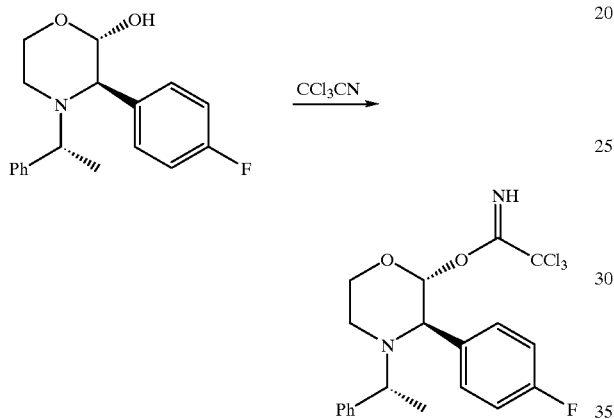

To the solution of crude N-((S)-(−)-α-Methylbenzyl)-2-hydroxy-3-(S)-(4-fluorophenyl)-1,4-oxazin-2-one (3.8L) was added K₂CO₃ (206 g), trichloroacetonitrile (447 mL) and DBU (4.5 mL). The resulting mixture was stirred at RT for 5 h. The solids were filtered off and washed with toluene (500 mL). The combined filtrates were concentrated to a total volume of 4.0 L in vacuo to yield a solution of crude trichloroimidate which was used directly for the next step.

EXAMPLE 11

Coupling of N-((S)-(-)-α-Methylbenzyl)-2-hydroxy-3-(S)-(4-fluorophenyl)-1,4-oxazin-2-one trichloroacetimidate with (R)-(3,5-bis(trifluoromethyl)phenyl)ethan-2-ol

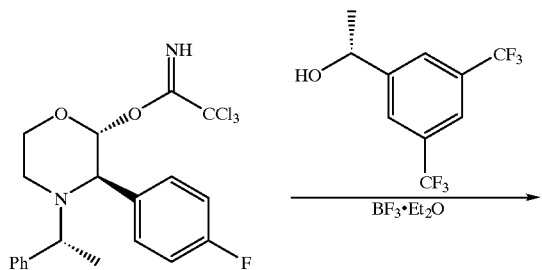

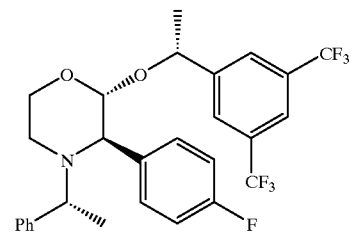

A solution of (R)-(3,5-bis(trifluoromethyl)phenyl)ethan-2-ol (769 g) in dry THF (7.0 L, KF<100 μg/mL) was cooled to −25° C. and BF₃.Et₂O (50.8 g) was added in portion. The solution of the trichloroimidate in toluene from the previous step was added slowly to maintain the temperature below −20 C. The reaction mixture was aged at −20° C. for 1 h and then quenched via addition of a mixture of 10% Na₂CO₃ solution and brine (0.6 and 2.4L, respectively). The organic layer was separated, concentrated to a total volume of approximately 3 L and then flushed with ethanol (2×3 L) in vacuo (40–50° C., 60 mmHg) at constant volume. Additional ethanol was added to dilute the mixture to a total volume of 8 L. The mixture was heated to 50° C. to effect complete dissolution of the crystals. Water (2 L) was added slowly over 2 h. The mixture was allowed to cool to ambient temperature and aged for 2 h. The solids were filtered, washed with a 3/1 mixture of ethanol/water (2 L) and dried to yield 1.85 kg of the trans-glycoside (80% overall yield from the oxazinone).

EXAMPLE 12

2-[1-[3,5-bis(trifluoromethyl)phenyl]ethoxy-3-(4-fluorophenyl)-1,4-oxazine

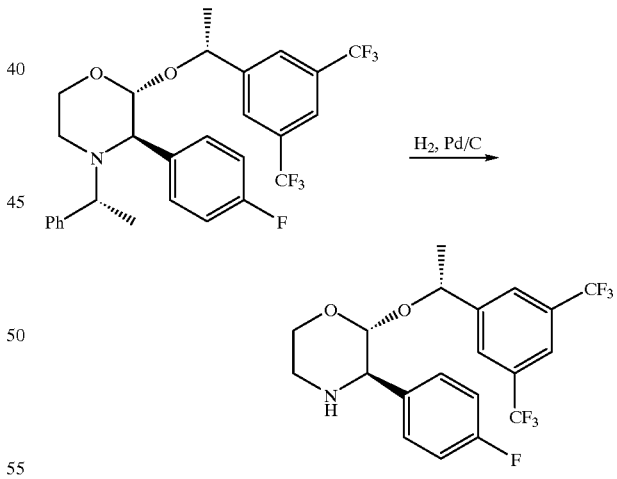

To a solution of the trans-glycoside (1.3 kg) in a mixture of toluene (3.5 L) and ethanol (3.5 L) was added 4-toluenesulfonic acid monohydrate (464 g) and 5% Pd/C (65 g). The mixture was hydrogenated at 40 psi of hydrogen and 20–30° C. for 3 h. The catalyst was removed via filtration over Solka-Floc. The filter bed was washed with a 1/1 mixture of toluene and ethanol (2 L). The combined filtrates were washed consecutively with a 5% solution of Na₂CO₃ (4 L) and water (3 L), and then used directly for the next step.

EXAMPLE 13

Dehydrogenation of 2-[1-[3,5-bis(trifluoromethyl)phenyl]ethoxy-3-(4-fluorophenyl)-1,4-oxazine

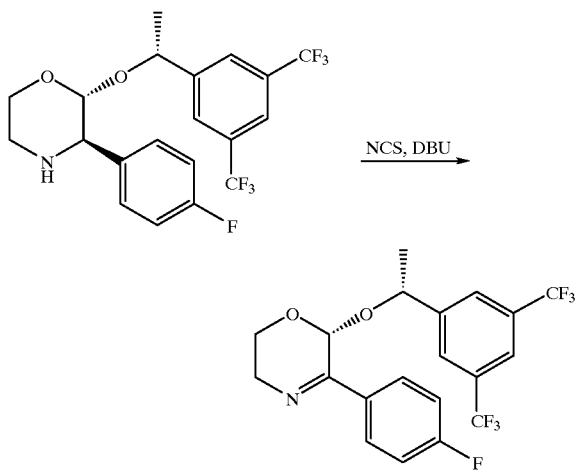

To the crude 2-[1-[3,5-bis(trifluoromethyl)phenyl] ethoxy-3-(4-fluorophenyl)-1,4-oxazine solution (approximately 6 L) was added DMF (0.6 L) and $K_2CO_3$ (66 g). The mixture was cooled to 0° C. and DBU (455 g) was added followed by N-chlorosuccinimide (367 g). The mixture was allowed to warm to ambient temperature over 2 h and aged for 3–5 h at this temperature before water (4 L) was added. The organic layer was separated and washed with additional water (4 L). The crude product solution was used directly for the next step.

EXAMPLE 14

(2R, 2-alpha-R, 3a)-2-[1-[3,5-bis(trifluoromethyl)phenyl]ethoxy-3-(4-fluorophenyl)-1,4-oxazine

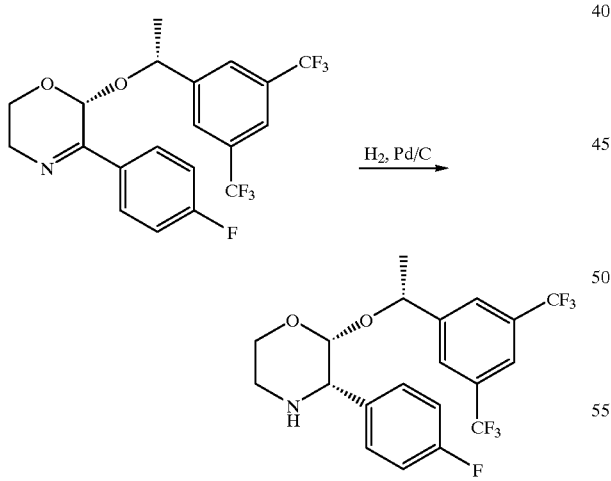

Ethanol (2.5 L) and 5% Pd/C (50 g) were added to the crude imine solution. The mixture was hydrogenated at 4.0 psi of hydrogen and ambient temperature for 2 h and then filtered over Solka-Floc to remove the catalyst. The filter bed was washed with toluene (3 L) and 4-toluenesulfonic acid monohydrate (455 g) was added to the filtrates. The mixture was partially concentrated to a total volume of approximately 6 L under a slight vacuum at 60–80° C. After seeding and slow cooling to ambient temperature heptane (2 L) was added. The solids were filtered and dried at 40° C. to yield (2R, 2-alpha-R, 3a)-2-[1-[3,5-bis(trifluoromethyl)phenyl]-thoxy-3-(4-fluorophenyl)-1,4-oxazine p-toluenesulfonate salt (94% overall yield from the trans-glycoside).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

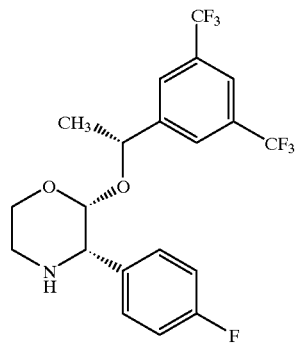

which comprises:

(1) contacting a compound of the formula:

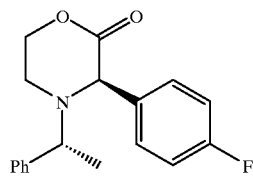

with a reducing agent to give a compound of the formula:

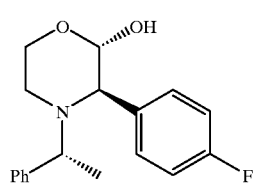

(2) activating such compound with an activating agent to give a compound of the formula:

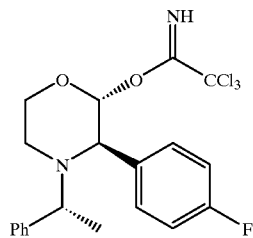

(3) coupling such activated compound with a compound of the formula:

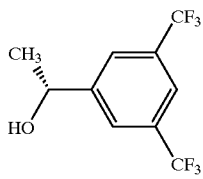

in the presence of a Lewis acid to give a compound of the formula:

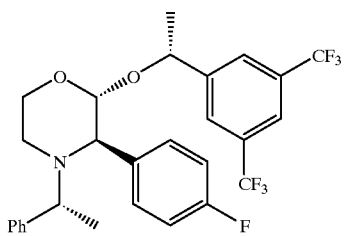

(4) hydrogenation of such compound to give a compound of the formula:

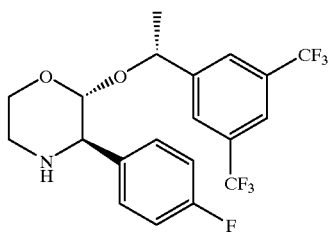

(5) dehydrogenation of such compound to give a compound of the formula:

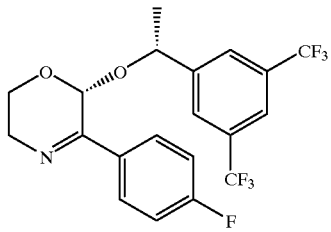

and (6) hydrogenation of such compound to give the compound of the formula:

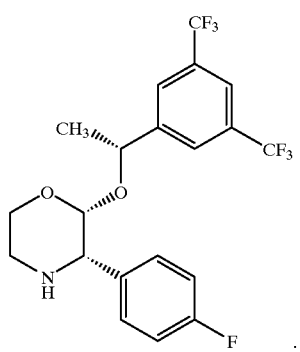

2. The process of claim 1 wherein Step (1) the reducing agent is di(iso-butyl)aluminum hydride (DIBAL).

3. The process of claim 1 wherein Step (1) is conducted in a solvent which comprises an organic solvent which is selected from toluene, tetrahydrofuran, diethyl ether, diglyme, and methyl t-butyl ether, and mixtures thereof, wherein tetrahydrofuran, toluene and mixtures thereof.

4. The process of claim 1 wherein Step (2) the activating agent is trichloroacetonitrile.

5. The process of claim 1 wherein Step (3) the activating agent is boron trifluoride etherate.

6. The process of claim 1 wherein Step (4) the hydrogenation is catalytic hydrogenation.

7. The process of claim 6 wherein Step (4) the hydrogenation catalyst is selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst).

8. The process of claim 6 wherein Step (4) the hydrogenation catalyst is palladium on carbon.

9. The process of claim 1 wherein Step (5) the dehydrogenation is conducted with dibromouricil (DBU) and N-chlorosuccinimide.

10. The process of claim 1 wherein Step (5) the dehydrogenation is conducted in a solvent which comprises dimethylformamide.

11. The process of claim 1 wherein Step (4) the hydrogenation catalyst is selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst).

12. The process of claim 1 wherein Step (4) the hydrogenation catalyst is palladium on carbon.

13. A process for the preparation of a compound of the formula:

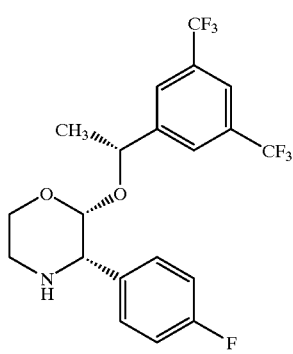

which comprises hydrogenation of a compound of the formula:

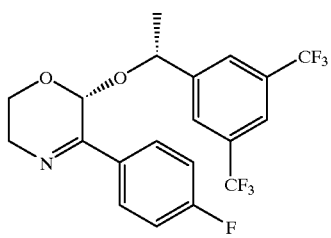

to give the compound of the formula:

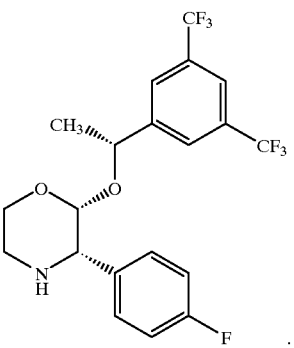

14. The process of claim 13 wherein the hydrogenation is catalytic hydrogenation.

15. The process of claim 14 wherein the hydrogenation catalyst is selected from: palladium on carbon, palladium on alumina, palladium on barium sulfate, palladium on calcium carbonate, palladium on barium carbonate, palladium on strontium carbonate, palladium on silica, and palladium hydroxide on carbon.

16. The process of claim 13 wherein the hydrogenation catalyst is palladium on carbon.

* * * * *